United States Patent [19]
Ogawa et al.

[11] Patent Number: 5,407,709
[45] Date of Patent: * Apr. 18, 1995

[54] ANTI-CONTAMINATING ADSORBED FILM AND METHOD OF MANUFACTURING THE SAME

[75] Inventors: Kazufumi Ogawa, Hirakata; Norihisa Mino, Settu; Mamoru Soga, Osaka, all of Japan

[73] Assignee: Matsushita Electric Industrial Co., Ltd., Osaka, Japan

[ * ] Notice: The portion of the term of this patent subsequent to Aug. 16, 2011 has been disclaimed.

[21] Appl. No.: 148,499

[22] Filed: Nov. 8, 1993

Related U.S. Application Data

[62] Division of Ser. No. 812,820, Dec. 24, 1991, Pat. No. 5,284,707.

[30] Foreign Application Priority Data

Dec. 25, 1990 [JP] Japan .................................. 2-405754
Jan. 23, 1991 [JP] Japan .................................. 3-024023

[51] Int. Cl.$^6$ ............................................. B05D 3/06
[52] U.S. Cl. .................................. 427/539; 427/529; 427/352; 427/341
[58] Field of Search ............... 427/387, 534, 535, 536, 427/537, 539, 352, 340, 341

[56] References Cited

U.S. PATENT DOCUMENTS

| | | | |
|---|---|---|---|
| 4,539,061 | 9/1985 | Sagiv | 156/278 |
| 4,902,585 | 2/1990 | Ogawa et al. | 428/694 |
| 5,010,356 | 4/1991 | Albinson | 346/140 R |

FOREIGN PATENT DOCUMENTS

| | | |
|---|---|---|
| 604002 | 8/1960 | Canada . |
| 0326438 | 8/1989 | European Pat. Off. . |
| 0367438 | 5/1990 | European Pat. Off. . |
| 0482613 | 4/1992 | European Pat. Off. . |
| 0491251 | 6/1992 | European Pat. Off. . |
| 805028 | 11/1958 | United Kingdom . |

*Primary Examiner*—Shrive Beck
*Assistant Examiner*—Erma Cameron
*Attorney, Agent, or Firm*—Fish & Richardson

[57] ABSTRACT

This invention provides for an anti-contaminating film which is adsorbed to a substrate surface. The film contains a —Si— group and fluorocarbon group. The —Si— group is covalently bonded to the substrate surface. It also provides a forming method of an anti-contaminating film on a hydrogen active substrate surface by contacting the substrate surface with a non-aqueous solution, containing a surface active material having fluorocarbon groups and chlorosilane groups, the substrate surface having active hydrogen groups, removing unreacted surface active material remaining on the substrate by washing the substrate with a non-aqueous organic solution for making a monomolecular precursor film, reacting chlorosilane groups unreacted in the adsorbed monomolecular a precursor film with water after the removing step, and drying the adsorbed monomolecular film.

6 Claims, 2 Drawing Sheets

ANTI-CONTAMINATING ADSORBED FILM AND METHOD OF MANUFACTURING THE SAME

This application is a divisional of U.S. application Ser. No. 07/812,820, filed Dec. 24, 1991, now U.S. Pat. No. 5,284,707.

FIELD OF THE INVENTION

This invention relates to an anti-contaminating film. More particularly, this invention relates to a film which is adsorbed to a substrate surface, said film preferably being a fluorine-based film. This invention further relates to a method for adsorbing film to the substrate surface.

BACKGROUND OF THE INVENTION

A monomolecular film may be formed by a chemical adsorption process of a chlorosilane-based surface active material having a long hydrocarbon chain to a substrate surface. The substrate can be aluminum or stainless steel and can have hydroxyl groups attached.

The method of adsorbing a film to a substrate surface involves a hydrochloric acid removal reaction. This reaction takes place between hydroxyl groups on a substrate surface and chlorosilyl groups of the chlorosilane-based surface active material.

The surface of an aluminum or a stainless steel substrate is rendered an anti-contaminating, heat-resistant, weather-resistant and wear-resistant by coating the substrate surface with a fluorocarbon-based thin film.

This is usually done by rendering the surface of an aluminum substrate coarse by means of a wire brush or chemical etching, coating with a primer and then with a paint. The paint is usually prepared by suspending fluorocarbon-based fine particles of ethylene polytetrafluoride in ethanol, drying, and then baking at about 400° C. for about one hour. The procedure fixes the fluorocarbon-based polymer to the substrate surface.

Known methods of adsorbing the chlorosilane-based surface active material, however, do not substantially increase the anti-contaminating property of the film.

Known methods of coating a fluorocarbon-based coating film, on the other hand, permit ready formation of the anti-contaminating film. However, there is a limit to the degree in which the polymer is anchored to the substrate. Therefore, the method is inadequate when used in manufacturing high mechanical strength apparatuses which require anti-contaminating, heat-resistant, weather-resistant and wear-resistant coatings. These apparatuses include, for example, hot plates, rice cookers and other electric products, vehicles, industrial machines, glass lenses, mirrors, etc.

Moreover, with the prior art coating method, a coating film thickness of several tens of microns is necessary at least in order to prevent pin-hole generation. Therefore prior art films lack transparency or brilliancy.

SUMMARY OF THE INVENTION

The present invention has been developed in light of the above drawbacks in the prior art.

An objective of the invention is to provide a monomolecular film and/or polymer film which is chemically adsorbed to a substrate surface. The film is anti-contaminating and transparent or brilliant. A method of manufacturing the same has also been developed, the film containing —St— groups and fluorine, wherein the —Si— groups are covalently bonded to the substrate surface.

Another objective of this invention is to provide a preparation method of an anti-contaminating monomolecular film to a substrate surface comprising:

contacting the substrate surface with a non-aqueous solution, said non-aqueous solution containing a surface active material having fluorine groups and chlorosilane groups, said substrate surface having active hydrogen groups;

removing unreacted surface active material remaining on the substrate by washing the substrate with a non-aqueous organic solution for making monomolecular precursor film;

reacting chlorosilane groups unreacted in the adsorbed monomolecular precursor film with water after the removing step; and drying the adsorbed monomolecular film.

Another objective of this invention is to provide a method of adsorbing an anti-contaminating polymer film to a substrate surface comprising:

contacting the substrate surface with a non-aqueous solution, said non-aqueous solution containing a surface active material having fluorocarbon-based groups and chlorosilane groups said substrate surface having active hydrogen groups;

reacting a precursor polymer film on the substrate surface which contains a silanol group by reacting the chlorosilane groups with water; and drying the adsorbed polymer film.

It is preferable in this invention that the adsorbed film is a fluorocarbon-based monomolecular film.

It is preferable in this invention that the adsorbed film is a fluorocarbon-based polymer film.

It is preferable in this invention that the substrate is selected from the group consisting of pottery, porcelain, ceramics, glass, stone, wood, and plastic.

It is preferable in this invention that the substrate contains surface active hydrogen groups.

It is preferable in this invention that the active hydrogen groups are selected from the group consisting of hydroxyl groups, amino groups, and imino groups.

It is preferable in this invention that the substrate surface made hydrophilic in advance of the contacting step by treating oxygen or nitrogen in a plasma or corona atmosphere.

It is preferable in this invention that the surface active material is

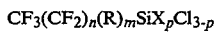

$$CF_3(CF_2)_n(R)_mSiX_pCl_{3-p}$$

where n represents 0 or an integer, R represents an alkylene group, vinylene group, ethynylene group, or a substituted group containing a silicon atom or an oxygen atom, m represents 0 or 1, X represents a hydrogen atom or a substituted group consisting of an alkyl group or an alkoxyl group, and p represents 0, 1 or 2.

According to the invention, the above problems can be solved by adsorbing a transparent, anti-contaminating film to a substrate surface. The film comprises a —Si— group which is covalently bonded to the substrate surface. The film also contains fluorine. According to the invention, by using a chemical adsorption method, a hydrophobic film having a uniform thickness in the nanometer range can be formed at the substrate surface without spoiling gloss and transparency. Thus, it is possible to provide a substrate which is highly hydrophobic, oil-phobic, substantially pin-hole free, heat resistant, durable brilliant, and contamination free.

The invention provides for a method which permits formation of a fluorocarbon-based monomolecular and/or polymer film which is in satisfactorily close contact with the substrate, is substantially pin-hole free and relatively thin. The invention, therefore, improves the performance of apparatuses which have heat-resistant, weather-resistant and wear-resistant coatings. Such apparatuses include, for example, hot plates, rice cookers and other electric products, vehicles, industrial apparatus, glass lenses and mirrors.

The method comprises following steps; contacting a hydrogen active substrate surface with a non-aqueous solution, said non-aqueous solution containing a surface active material having fluorine group and chlorosilane group, removing the unreacted surface active material remaining on the substrate by washing the substrate with a non-aqueous organic solution (when this process is omited, a fluorine-based adsorbed polymer film is made on to the substrate), forming a monomolecular or polymer precursor film containing a silanol group at the substrate surface by reacting the chlorosilane groups with water after the removing step, and drying the precursor film.

According to the invention, active hydrogen groups are exposed at the substrate surface. The active hydrogen groups are preferably hydroxyl groups, amino groups, or imino groups. Such groups are preferred because they participate readily in a dehydrochloric acid reaction with the chlorosilyl groups of the surface active material.

Thus can be used as the substrate to select from the group consisting of pottery, porcelain, ceramics, glass, stone, wood, and plastic.

A plastic or like material which does not have any oxide film on its surface can be also used as a substrate. The surface may be rendered hydrophilic, i.e., hydroxyl groups may be introduced by treating the surface with oxygen in a plasma or corona atmosphere. For example, the surface can be treated at 100 W for 20 minutes.

It is not necessary, however, to surface treat plastics having imino (=NH) groups such as polyamide or polyurethane substrates. Because imino groups have active hydrogen, it is relatively easy to reduce the groups by initiating the dehydrochloric acid reaction with the chlorosilyl groups of the surface active material.

The solution containing the material with a chlorosilyl group may, for example, be a non-aqueous solution containing chloroform etc.

The concentration of the non-aqueous solution which contains a surface active material having a chlorosilyl group may vary. However, a solution may be prepared, for example, by dissolving about one per cent by weight of the material to be used into solution. The substrate can be dipped into this solution and held for about 30 minutes to 2 hours. A hydrochloric acid removal reaction proceeds at the substrate surface due to the presence of hydrophilic (—OH) groups. An adsorbed film having material containing a silyl group is thereby formed. A monomolecular adsorbed film is then formed by removing the unreacted surface active material remaining on the substrate. The material is removed by washing the substrate with a non-aqueous organic solution. The step of washing the substrate surface using a non-aqueous organic solution process can be omited, however, when a fluorine-based polymer film is adsorbed to the substrate surface.

BRIEF DESCRIPTION OF THE DRAWINGS

This invention is described in detail with reference to the following drawings.

DETAILED DESCRIPTION OF THE INVENTION

Figure 1A:
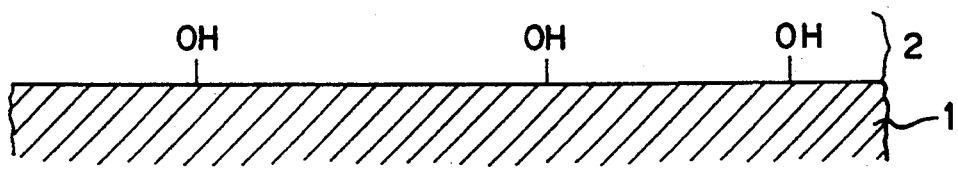
FIGS. 1(a) and 1(b) are molecular scale schematic sectional views showing a process as described in Example 1.

This invention provide a film which is adsorbed to a substrate surface. The film contains a —Si— group and fluorine. The —Si— group is covalently bonded to the substrate surface. It also provide a method of adsorbing an anti-contaminating film to the substrate surface having active a hydrogen by contacting the substrate surface with a non-aqueous solution containing a surface active material having a fluorocarbon group and a chlorosilane group, removing the unreacted surface active material remaining on the substrate by washing the substrate with a non-aqueous organic solution, adsorbing a precursor film having a silanol group to the substrate surface by reacting the chlorosilane group with water after the removing step, and drying the adsorbed precursor film.

The above washing step with the non-aqueous organic solution was omitted, fluorocarbon polymer film was formed to the substrate surface.

Examples of especially preferred fluorine-based surface active materials are those represented by the formula;

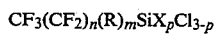
$CF_3(CF_2)_n(R)_mSiX_pCl_{3-p}$ where n represents 0 or an integer, R represents an alkyl group, vinylene group, ethynylene group, or a substituted group containing a silicon atom or an oxygen atom, m represents 0 or 1, X represents a hydrogen atom or a substituted group consisting of an alkyl group or an alkoxyl group, and p represents 0, 1 or 2.

These fluorochlorosilane-based surface active materials are suitably those represented by the formula;

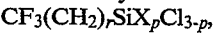
$CF_3(CH_2)_rSiX_pCl_{3-p}$,
$CF_3(CF_2)_sO(CH_2)_tSiX_pCl_{3-p}$,
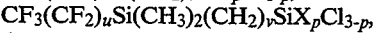
$CF_3(CF_2)_uSi(CH_3)_2(CH_2)_vSiX_pCl_{3-p}$,
and
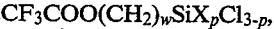
$CF_3COO(CH_2)_wSiX_pCl_{3-p}$, where r is from 1 to 25, s is from 0 to 12, t is from 1 to 20, u is from 0 to 12, v is from 1 to 20, w is from 1 to 25. These surface active materials are suitably represented by the following examples:

$CF_3CH_2O(CH_2)_{15}SiCl_3$,
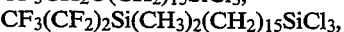
$CF_3(CF_2)_2Si(CH_3)_2(CH_2)_{15}SiCl_3$,
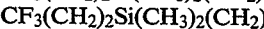
$CF_3(CH_2)_2Si(CH_3)_2(CH_2)_{15}SiCl_3$,
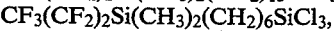
$CF_3(CF_2)_2Si(CH_3)_2(CH_2)_6SiCl_3$,
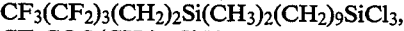
$CF_3(CF_2)_3(CH_2)_2Si(CH_3)_2(CH_2)_9SiCl_3$,
$CF_3COO(CH_2)_{15}SiCl_3$,
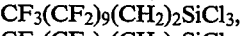
$CF_3(CF_2)_9(CH_2)_2SiCl_3$,
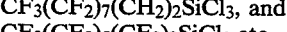
$CF_3(CF_2)_7(CH_2)_2SiCl_3$, and
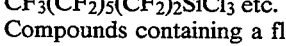
$CF_3(CF_2)_5(CF_2)_2SiCl_3$ etc.

Compounds containing a fluorine group and a chlorosilyl group may be used to impart desirable properties, i.e., they provide a film which is anti-contaminating, transparent, hydrophobic, oil-repelling and which may act as a lubricant.

The film according to the invention can be formed and maintained as a ultra thin film.

The invention can widely be applied to the following surfaces. Materials made of pottery, porcelain, ceramics, glass, plastic, wood, or stone etc. are applicable as the substrate. The surface of the substrate may be also coated with paint or the like in advance.

Examples of ceramics cutlery: a kitchen knife, scissors, a knife, a cutter, a graver, a razor, hair clippers, a saw, a plane, a chisel, a gimlet, a badkin, bite (cutting tools), a edge of a drill, a edge of a mixer, a juicer, a blade of a mill, a blade of a lawn mower, a punch, a straw cutter, a staple of a stapler, a can opener or a surgical knife and the like.

Examples of products in the pottery industry: products made of pottery, glass, ceramics or enameled products. For example, sanitary potteries (a chamber pot, a wash-bowl, a bathtub, etc.), tableware (a rice-bowl, a teacup, a dish (plate), a bowl, a teacup, a glass, a bottle, a coffee-pot (siphon), a pan, an earthenware mortar, (a cup and the like), vases (a flower bowl, a flowerpot, a bud vase and the like), water tanks (a breeding cistern, an aquarium water tank and the like), chemical experiment appliances (a beaker, a reactor vessel, a test tube, a flask, a laboratory dish, condenser, a mixing rod, a stirrer, a mortar, a bat, a syringe, etc.) a bath tile, a roof tile, enameled ware, an enameled washbowl, an enameled kettle, an enameled pan and the like.

Examples of ceramics molding parts: dies for press molding, dies for cast molding, dies for injection molding, dies for transfer molding, dies for compression molding, dies for transfer molding, dies for inflation molding, dies for vacuum molding, dies for blow forming, dies for extrusion molding, dies for fiber spinning, a calendar processing roll and the like.

Examples of plastics or ceramics forming molds for food: cake, cookies, bread-baking, chocolate, jelly, ice cream, oven ware, ice trays and the like.

Examples of resin(s): a polyolefin such as a polypropylene and polyethylene, a polyvinylchloride plastic, a polyamide, a polyimide, a polyamideimide, a polyester, an aromatic polyester, a polycarbonate, a polystyrene, a polysulfide, a polysulfone, a polyethersulfone, a polyphenylenesulfide, a phenolic resin, a furan resin, a urea resin, a epoxy resin, a polyurethane, a silicon resin, an ABS resin, a methacrylic resin, an acrylate resin, a polyacetal, a polyphenylene oxide, a polymethylpentene, a melamine resin, an alkyd resin, an unsaturated polyester cured resin and the like.

Examples of rubber: a styrene-butadiene rubber, a butyl rubber, a nitril rubber, a chloroprene rubber, a polyurethane rubber, a silicon rubber and the like.

Examples of ceramics, plastic or resin coating household electric appliances: a refrigerator, a freezer, an air conditioner, a juicer, a mixer, a blade of an electric fan, a lighting apparatus, a dial plate, a dryer for a perm and the like.

Examples of plastic sporting goods: skis, a fishing rod, a pole for the pole vault, a boat, a yacht, a surfboard, a fishing line, a float and the like.

Examples applying to vehicle parts:
(1) ABS resin: a lamp cover, an instrument panel, trimming parts, a protector for a motorcycle.
(2) Cellulose plastic: a car mark, a steering wheel
(3) FRP (fiber reinforced plastics): a bumper, an engine cover (jacket)
(4) Phenolic resin: a brake
(5) Polyacetal: wiper gear, a gas valve
(6) Polyamide: a radiator fan
(7) Polyarylate (polycondensation polymerization by bisphenol A and pseudo phthalic acid): a direction indicator lamp lens), a cowl board lens, a relay case
(8) Polybutylene terephthalate (PBT): a rear end, a front fender
(9) Poly amino-bismaleimide: engine parts, a gear box, a wheel, a suspension drive system
(10) Methacrylate resin: a lamp cover lens, a meter panel and its cover, a center mark
(11) Polypropylene: a bumper
(12) Polyphenylene oxide: a radiator grill, a wheel cap
(13) polyurethane: a bumper, a fender, an installment panel, a fan
(14) Unsaturated polyester resin: a body, a fuel tank, a heater housing, a meter pannel.

Examples of plastic or resin coating office supplies: a desk, a chair, a bookshelf, a rack, a telephone stand table, a rule (measure), a drawing instrument and the like.

Examples of building materials: materials for a roof, an outer wall and interiors. Roof materials such as brick, slate and the like. Outer wall materials such as wood (including processed manufactured wood), mortar, concrete, ceramic sizing, brick, stone, and plastic. Interior materials such as wood (including processed wood), plastic, a paper and the like.

Examples of building stones: granite, marble and others for use as a building, a building material, an architectural fixture, an ornament, a bath, a grave stone, a monument, a gatepost, a stone wall, a paving stone and the like.

Specific examples of the process of chemical adsorption of a water-repelling oil-repelling anti-fogging, anti-contaminating film coating according to the invention will now be described with reference to FIGS. 1 and 2.

EXAMPLE 1

The glass of a car door mirror having a processed real image side surface was washed with an organic solvent. A solution (non-aqueous solvent) containing 80% wt n-hexadecane, 12% wt carbon tetrachloride and 8% wt chloroform was prepared by using $CF_3(CF_2)_7(CH_2)_2$—$SiCl_3$ as a silane surface active material and dissolving the same at a concentration of 2% wt. A glass substrate 1, i.e., a car door mirror as shown in FIG. 1(a), was dipped into this solution and held at room temperature for one hour. Since the surface of the substrate 1 contained hydroxyl group 2, a reaction between the chlorosilyl group of the chlorosilane-based surface active material and the hydroxyl group occur to form covalent bond on the surface. This reaction is represented in the following formula [1].

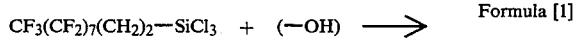

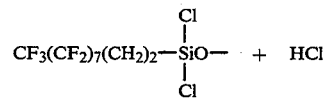 + HCl

Formula [1]

The glass mirror 1 was then washed by freon 113 to remove the unreacted material remaining on the surface, followed by washing with water or exposing to air containing moisture. The —SiCl group was changed to a —SiOH group as in formula [2].

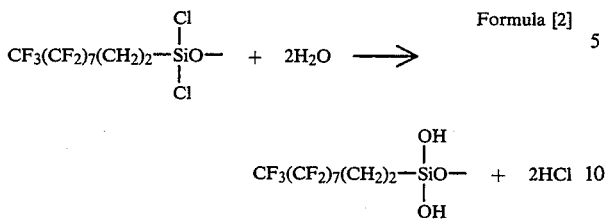

Each silanol group (—SiOH) was then dehydrated and crosslinked to form a siloxane bond (—SiO—) after drying as in formula [3]. Drying temperature may be room temperature or above.

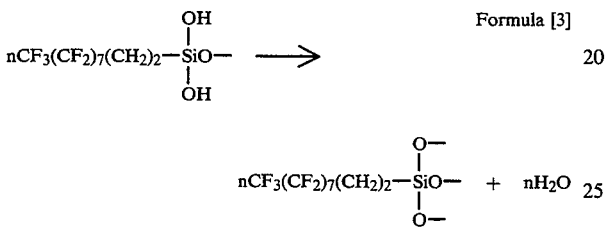

Figure 1B:
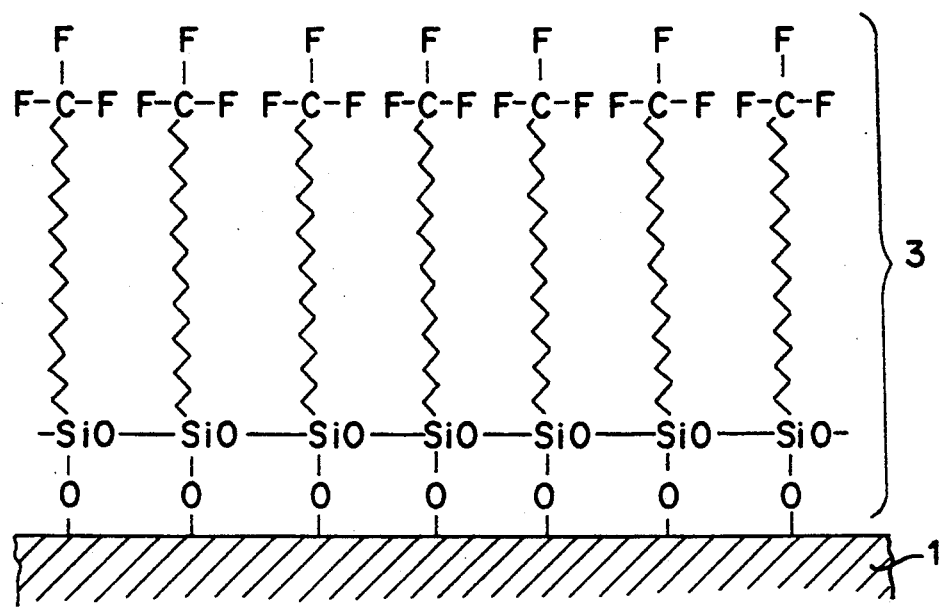

An adsorbed monomolecular film 3 could be obtained on the surface of the glass substrate 1 as shown FIG. 1(b). The adsorbed monomolecular film 3 has a fluorine group and is chemically bonded (i.e., covalently bonded) to the substrate 1. The chemical bond is via a siloxane bond. The formation of chemically adsorbed monomolecular film 3 was assumed by FTIR spectrometry and the thickness was about 1.5 nanometers (nm). It is firmly bonded such that it will not separate.

The treated mirror was compared to a mirror which was not treated. The treated mirror greatly reduced contaminant adherence. In addition, any contaminant which did remain on the treated mirror could be readily removed by wiping with a brush or the like. This could be done without causing any scar or scratch on the glass surface.

In the above example, only the door mirror glass was treated. However, by chemically adsorbing a monomolecular film to a whole door mirror, the same anti-contaminating effect could be obtained on the frame part of the door mirror as well. Any contaminants remaining on the frame could be also readily wiped off.

The above washing step with the non-aqueous organic solution (freon 113) was omitted, and a fluorine-based polymer film was adsorbed to the substrate surface. The fluorocarbon-based polymer film was satisfactorily close adhere to the substrate. The film was substantially pin-hole free, thin, anti-contaminating, transparent and brilliant.

EXAMPLE 2

Figure 2A:
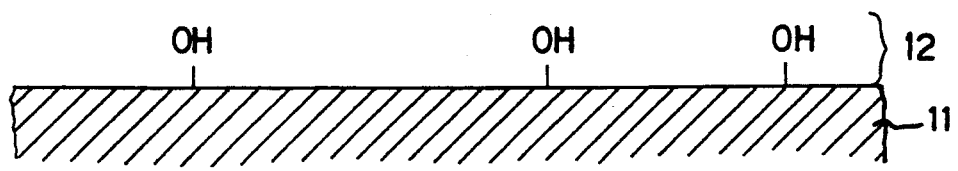
FIGS. 2(a) and 2(b) are molecular scale schematic sectional views showing a process as described in Example 2.

A solution was prepared by using $$CF_3(CF_2)_9(CH_2)_2-SiCl_3$$

as a silane surface active material and dissolving the same in freon 113 to a concentration of 2% wt. A coffee cup as a porcelain substrate 11, as shown in FIG. 2(a), was dipped into this solution and held at room temperature for one hour, and then the substrate was washed by "Fluorinert FC72" (products by 3M corp., fluorin-based solution). Since the surface of the substrate 11 contained hydroxyl group 12, a reaction between the chlorosilyl group of the chlorosilane-based surface active material and the hydroxyl group occured as represented in the formula [4]. This reaction proceeded substantially the same as above in formulas [1] to [3].

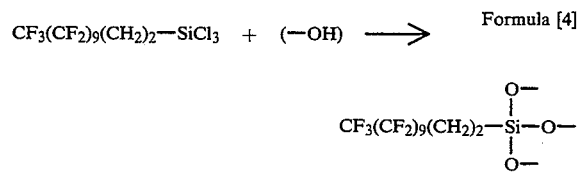

Figure 2B:
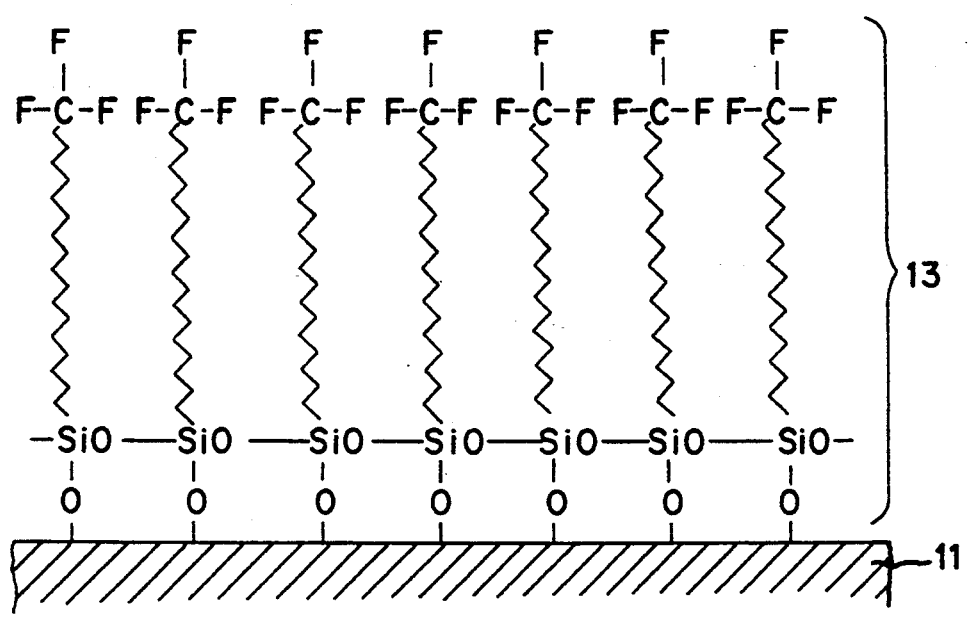

An adsorbed monomolecular film 13 was obtained on the surface of the porcelain substrate 11 as shown FIG. 2(b). The adsorbed monomolecular film 13 has a fluorine group and is chemically bonded (i.e., covalently bonded) to the substrate 11. The chemical bond is via a —Si— covalent bond. This chemically adsorbed monomolecular film 13 was assumed by FTIR spectrometry and the thickness was about 1.5 nanometers (nm). It is firmly bonded such that it will not separate.

The treated porcelain substrate was compared to an unreacted or untreated porcelain substrate. The treated substrate greatly reduced contaminant adherence. In addition, any contaminant which did remain on to the treated substrate could be readily removed by wiping with a brush or the like. This could be done without causing any scar or scratch on the porcelain surface.

The above washing step with the "Fluorinert FC72" was omitted, and a fluorocarbon polymer film was adsorbed to the substrate. The fluorocarbon-based polymer film was in satisfactorily close contact with the substrate. The film was substantially pin-hole free, thin, anti-contaminating, transparent and brilliant.

EXAMPLE 3

A polycarbonate substrate 5 cm on each side and 0.3 cm in thickness was used as a polymer substrate. Its surface was oxidized by oxygen plasma treatmenting for 10 minute with a UV dry stripper ("UV-1" by Samco International) at an oxygen supply rate of 1 l/min. Then, in a nitrogen atmosphere and at room temperature, the treated substrate was dipped and held for 60 minutes in a freon 113 solution containing heptadecafluorodecyl-trichlorosilane at concentration of $10^{-2}$ mol/l as a chlorosilane-based surface active material having fluoroalkyl groups. Then, non-reacted heptadecafluorodecyl-trichlorosilane was washed out by using freon 113 and then water. A chemically adsorbed monomolecular film containing fluoroalkyl groups bonded via siloxane bonds to the polycarbonate substrate surface was formed.

The adsorbed monomolecular film has a fluorine atoms and is chemically bonded (i.e., covalently bonded) to the substrate via a siloxane bond. This chemically adsorbed monomolecular film was assumed by FTIR spectrometry and the thickness was about 1.5 nanometers (nm). It firmly bonded such that it will not separate.

The treated polycarbonate substrate was compared to an untreated polycarbonate substrate. The treated substrate greatly reduced contaminant adherence. In addition, any contaminant which did remain on the treated substrate surface could be readily removed by wiping with a brush or the like. This could be done without causing any scar or scratch on the polycarbonate surface.

The above washing step with the non-aqueous organic solution (freon 113) was omitted, and a fluorine-based polymer film was adsorbed to the substrate. The fluorocarbon-based polymer film was in satisfactorily close adhere to the substrate. The film was substantially pin-hole free, thin, anti-contaminating, transparent and brilliant.

The contact angle of each of the samples of Examples 1 to 3 with respect to super-pure water and to salad oil was examined. It was measured immediately after the formation of the film and after subsequently rubbing the surface 10,000 times with cloth wetted with water. Table 1 shows the results.

TABLE 1

|  | Contact angle (°) with respect to water | | Contact angle (°) with respect to salad oil | |
| --- | --- | --- | --- | --- |
|  | Initial value | After test | Initial value | After test |
| Example 1 | 112 | 109 | 92 | 90 |
| Example 2 | 111 | 109 | 93 | 91 |
| Example 3 | 110 | 108 | 91 | 89 |

EXAMPLE 4

A bath tile as a pottery was washed with an organic solvent and then dipped and held for about two hours in a non-aqueous solution containing a material having a fluorocarbon group and a chlorosilane group. The solution contained 80% wt n-hexadecane (or toluene or xylene or dicyclohexyl), 12% wt carbon tetrachloride and 8% wt chloroform. The solution was prepared by dissolving;

$CF_3(CF_2)_5(CH_2)_2SiCl_3$ 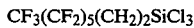

at a concentration of about 1% wt. The tile contains many hydroxyl groups on the surface. Therefore, a hydrochloric acid removal reaction was brought about between the —SiCl groups and the hydroxyl groups to produce covalent bonds on the entire surface as in formula [5]. This reaction proceeded substantially the same as above in formulas [1] to [3].

$CF_3(CF_2)_5(CH_2)_2SiCl_3 + (-OH)$ 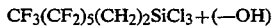

$$\longrightarrow CF_3(CF_2)_5(CH_2)_2Si\begin{matrix}O-\\|\\-O-\\|\\O-\end{matrix}$$ Formula [5]

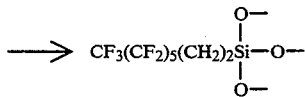

A fluorine-containing monomolecular film was formed at a thickness of about 1.5 nm on the tile substrate surface such that it was chemically bonded to the surface. This monomolecular film did not separate in a checkerboard test.

The coated tile was used in bath room. The bath tile greatly reduced contaminant adherence, and the tile was clean surface.

The above washing step with the non-aqueous organic solution (freon 113) was omitted, and a fluorine-based polymer film was adsorbed to the substrate. The fluorocarbon-based polymer film was in satisfactorily close adhere to the substrate. The film was substantially pin-hole free, thin, anti-contaminating, transparent and brilliant.

EXAMPLE 5

A sintered kettle (pot) or bowl (hereinafter referred to as porcelain) was prepared. Then, the porcelain was washed with an organic solvent and dipped and held for about two hours in a non-aqueous solution containing a material with a fluorocarbon group and a chlorosilane group in molecule. The solution contained 80% wt n-hexadecane (or toluene or xylene or dicyclohexyl), 12% wt carbon tetrachloride and 8% wt chloroform. The solution was prepared by dissolving; $CF_3(CF_2)_3(CH_2)_2Si(CH_3)_2(CH_2)_9SiCl_3$ at a concentration of about 1% wt. The porcelain (as well as a $Al_2O_3$ ceramics etc.) has many hydroxyl groups on the surface. Therefore, a hydrochloric acid removal reaction was brought about between the —SiCl groups and the chlorosilane groups to produce bonds over the entire porcelain surface. This reaction proceeded substantially the same as above in formulas [1] to [3]. $CF_3(CF_2)_3(CH_2)_2Si(CH_3)_2(CH_2)_9Si(O-)_3$ 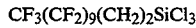

A fluorine-containing monomolecular film chemically bonded at the surface was formed to a thickness of about 1.5 nm on the porcelain substrate surface. This monomolecular film did not separate in a checkerboard test.

The coated pot was used. Any contaminants attached could be reduced greatly compared to that attached to an untreated pot. In addition, any remaining contaminants were readily removed by brushing the surface with a washing brush. This was done without causing any scar or scratch. Fatty matter and rice particles were removed by washing the bowl with water. Further, tannin of tea hardly attached.

The above washing step with a non-aqueous organic solution (freon 113) was omitted, and a fluorine-based polymer film was adsorbed to the substrate. The fluorocarbon-based polymer film was satisfactorily close adhere to the substrate. The film was substantially pin-hole free, thin, anti-contaminating, transparent and brilliant.

EXAMPLE 6

A processed flooring marble was prepared. The marble was washed with an organic solvent and then dipped for about two hours in a non-aqueous solution containing a material with a fluorocarbon group and a chlorosilane group in molecule. The solution contained 80% wt n-hexadecane (or toluene or xylene or dicyclohexyl), 12% wt carbon tetrachloride and 8% wt chloroform. The solution was prepared by dissolving;

$CF_3(CF_2)_9(CH_2)_2SiCl_3$ at a concentration of about 1% wt. The marble (as well as other stones) contains many hydroxyl groups on the surface. Therefore, a hydrochloric acid removal reaction was brought about between the —SiCl groups and the hydroxyl groups to produce covalent bonds on the entire marble surface. This reaction proceeded substantially the same as above in formulas [1] to [3].

$CF_3(CF_2)_9(CH_2)_2Si(O-)_3$ 

A fluorine-containing monomolecular film was formed at a thickness of about 1.5 nm on the marble substrate surface such that it was chemically bonded to the surface. This monomolecular film did not separate in a checkerboard test.

The above washing step with a non-aqueous organic solution (freon 113) was omitted, and a fluorine-based polymer film was adsorbed to the substrate. The fluorocarbon-based polymer film was in satisfactorily close adhere to the substrate. The film was substantially pinhole free, thin, anti-contaminating, transparent and brilliant.

The coated marble was used floor. It greatly reduced adherence of contaminants compared to an untreated marble. The marble was clean surface. In addition, any remaining contaminants could be readily removed by brushing the contaminated surface with a brush. This could be done without causing any scar or scratch.

As has been described in the foregoing, the invention concerns a chemically adsorbed film, which comprises a chemically adsorbed monomolecular and/or polymer film formed on a substrate surface via a —Si— covalent bonds, and a method of manufacturing a chemically adsorbed film, which comprises a film chemically adsorbed to the substrate surface, and a method of adsorbing a monomolecular film, which comprises contacting a hydrogen active substrate surface with a non-aqueous solution containing a surface active material having a fluorocarbon group and a chlorosilane group, removing untreated surface active material remaining on the substrate by washing the substrate with a non-aqueous organic solution (when this process is omited, a fluorocarbon polymer film is adsorbed the substrate), forming a precursor film containing a silanol group at the substrate by reacting the chlorosilane groups with water after the removing step, and drying the precursor film. Thus, it is possible to obtain an effective chemically adsorbed monomolecular film which will readily adsorb to pottery, porcelain, ceramics, glass, stone, wood, and plastic substrates which have active hydrogen groups at their surface. Where by using a compound containing a fluorocarbon group and a chlorosilyl group, a fluorocarbon-based film having excellent hydrophilic, oil-repelling, anti-contaminating properties could be formed on the substrate. The film is chemically bonded to the substrate, is at a high density, is substantially pin-hole free, and has a thin uniform thickness. It is thus anti-contaminating and brilliant possible to provide a highly durable, high performance, super-thin, fluorocarbon-based film.

As has been shown, the invention is greatly beneficial to industry.

The invention may be embodied in other specific forms without departing from the spirit or essential characteristics thereof. The present embodiment is to be considered in all respects as illustrative and not restrictive, the scope of the invention being indicated by the appended claims rather than by the foregoing description and all changes which come within the meaning and range of equivalency of the claims are intended to be embraced therein.

We claim:

1. A method of adsorbing an anti-contaminating monomolecular film to a substrate surface comprising:

reacting the substrate surface with a non-aqueous solution, said non-aqueous solution containing a surface active material having fluorocarbon groups and chlorosilane groups, said substrate surface having active hydrogen groups;

reacting unreacted surface active material remaining on the substrate by washing the substrate with a non-aqueous organic solution, thereby making an adsorbed monomolecular precursor film;

reacting chlorosilane groups unreacted in the adsorbed monomolecular precursor film with water after the removing step, thereby making an adsorbed monomolecular film; and drying the adsorbed monomolecular film.

2. The method of adsorbing an anti-contaminating film according to claim 1, wherein said substrate surface is made hydrophilic prior to said first reacting step by introducing oxygen or nitrogen in a plasma or corona atmosphere.

3. The method of adsorbing an anti-contaminating film according to claim 1, wherein said surface active material is $$CF_3(CF_2)_n(R)_mSiX_pCl_{3-p}$$

wherein n represents 0 or an integer, R represents an alkylene group, vinylene group, ethynylene group, a substituted group containing a silicon atom, or a substituted group containing an oxygen atom, m represents 0 or 1, X represents a hydrogen atom or a substituted group consisting of an alkyl group or an alkoxyl group, and p represents 0, 1 or 2.

4. A method of adsorbing an anti-contaminating polymer film to a substrate surface comprising:

reacting the substrate surface with a non-aqueous solution, said non-aqueous solution containing a surface active material having fluorine groups and chlorosilane groups, said substrate surface having active hydrogen groups;

forming an absorbed polymer film on the substrate surface, which surface contains a silanol group, by reacting the chlorosilane groups with water: and drying said adsorbed polymer film.

5. The method of adsorbing an anti-contaminating polymer film according to claim 4, wherein said substrate surface is made hydrophilic prior to said reacting step by introducing oxygen or nitrogen in a plasma or corona atmosphere.

6. The method of adsorbing an anti-contaminating polymer film according to claim 4, wherein said surface active material is $$CF_3(CF_2)_n(R)_mSiX_pCl_{3-p}$$

where n represents 0 or an integer, R represents an alkylene group, vinylene group, ethynylene group, or a substituted group containing a silicon atom or an oxygen atom, m represents 0 or 1, X represents a hydrogen atom or a substituted group consisting of an alkyl group or an alkoxyl group, and p represents 0, 1 or 2.

* * * * *